(12) United States Patent
Lindop et al.

(10) Patent No.: US 8,416,301 B2
(45) Date of Patent: Apr. 9, 2013

(54) STRAIN IMAGE DISPLAY SYSTEMS

(75) Inventors: Joel Edward Lindop, Cambridge (GB); Graham Michael Treece, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 0 days.

(21) Appl. No.: 12/598,349

(22) PCT Filed: Apr. 24, 2008

(86) PCT No.: PCT/GB2008/050293
§ 371 (c)(1), (2), (4) Date: Feb. 8, 2010

(87) PCT Pub. No.: WO2008/132504
PCT Pub. Date: Nov. 6, 2008

(65) Prior Publication Data
US 2010/0134629 A1 Jun. 3, 2010

(30) Foreign Application Priority Data
May 1, 2007 (GB) .................................. 0708358.7

(51) Int. Cl.
*G01S 15/89* (2006.01)
*G06K 9/00* (2006.01)

(52) U.S. Cl. ........................................ 348/163; 382/128

(58) Field of Classification Search .................. 348/163, 348/169, 218, 223, 36, 37, 39, 222.1, 213; 382/128, 103, 107, 100, 135, 173, 145, 284, 382/223, 218, 260, 130; 600/443, 447, 437, 600/438, 449
See application file for complete search history.

(56) References Cited

U.S. PATENT DOCUMENTS

| | | | |
|---|---|---|---|
| 6,558,324 B1 * | 5/2003 | Von Behren et al. ......... 600/440 |
| 2003/0163044 A1 | 8/2003 | Heimdal et al. | |
| 2006/0173320 A1 * | 8/2006 | Radulescu ................... 600/438 |
| 2008/0144902 A1 * | 6/2008 | Radulescu ................... 382/130 |
| 2009/0221916 A1 * | 9/2009 | Konofagou et al. ......... 600/443 |
| 2010/0251820 A1 * | 10/2010 | Righetti et al. ................. 73/602 |
| 2011/0204893 A1 * | 8/2011 | Sumi ............................ 324/318 |

FOREIGN PATENT DOCUMENTS

| EP | 0843181 A | 5/1998 |
|---|---|---|
| EP | 1647837 A | 4/2006 |
| WO | WO 2006/065615 A | 6/2006 |
| WO | WO 2007/110669 A1 | 10/2007 |
| WO | WO 2007/135450 A2 | 11/2007 |

OTHER PUBLICATIONS

International Search Report for corresponding PCT/GB2008/050293 completed Jul. 8, 2008 by Terhi Pohjamo of the EPO.

(Continued)

*Primary Examiner* — Behrooz Senfi

(57) ABSTRACT

A method of displaying strain image data for an imaged object, the method comprising: capturing strain image data defining deformation of said object over an imaged region of said object; processing said strain image data to determine local image quality data, said local image quality data comprising a measure of the quality of said strain image data varying over said imaged region; and displaying a representation of said strain image data for said imaged region of said object, using said local image quality data to provide a visual indication of the quality of said displayed representation varying over said imaged region or to improve a quality of said displayed representation of said strain image data.

30 Claims, 11 Drawing Sheets

OTHER PUBLICATIONS

Lindop, et al.: "*Estimation of Displacement Location for Enhanced Strain Imaging*"; Technical Report CUED/F-INFENG/TR 550, Cambridge University Department of Engineering, Mar. 2006.

Lindop, et al.: "*Dynamic Resolution Selection in Ultrasonic Strain Imaging*"; Technical Report CUED/F-INFENG/TR 566, Cambridge University Department of Engineering, Sep. 2006.

Lindop, et al.: "*Phase-Based Ultrasonic Deformation Estimation*"; Technical Report CUED/F-INFENG/TR 555, Cambridge University Department of Engineering, May 2006.

Computerized Imaging Reference Systems, Inc.; http://www.cirsinc.com; Model 052.

* cited by examiner (a) (b)

(c) (d)

STRAIN IMAGE DISPLAY SYSTEMS

FIELD OF THE INVENTION

This invention relates to methods, apparatus and computer program code for displaying strain images.

BACKGROUND TO THE INVENTION

Ultrasonic strain imaging is an emerging technique, which is likely to have numerous applications in the clinical examination of soft tissues. Here we are primarily (but not exclusively) interested in the subset of elasticity imaging techniques that are often grouped together as "static" (or "quasistatic") strain imaging. In this paradigm, small tissue deformations are caused by contact with the ultrasound probe at the tissue surface; two or more ultrasound frames are recorded during this deformation, and some form of tracking is applied to the recorded ultrasound data to estimate tissue deformations, amounting to spatially-varying displacement fields. Spatial derivatives of such a displacement field are tissue strain, which indicates stiffness: there are sometimes further stages of analysis to estimate quantitative tissue properties directly, such as elastic moduli. Techniques of this kind were first tested clinically for breast scanning and breast screening has ever since been a key driver for research. Numerous studies have been motivated by prostate screening. Detection and staging of deep vein thrombosis also seems particularly promising, and there are many other possible applications.

It is helpful at this point to introduce some of the terminology generally used in ultrasound imaging. An ultrasound imaging system generally employs a one-dimensional or two-dimensional ultrasonic transducer array (although sometimes only a single transducer may be employed), the array comprising typically 20 to 256 transducers in each dimension. Each transducer acts as both a transmitter and a receiver. The transducers are generally driven by a pulse of RF energy, typically in the range 1-20 MHz; the signal may be considered narrow band in the sense that a pulse is sufficiently long to include a number of RF wavelengths thus having a relatively well-defined frequency. The ultrasound transducer array is usually coupled to the tissue under investigation by an ultrasound gel or water; typically the ultrasound penetrates a few centimetres, for example up to 25 cm, into the tissue under investigation, and the transducer array scans a region of a few centimetres in a lateral direction. The axial resolution is generally much greater than the lateral resolution, for example of the order of 1000 samples (in time) as compared with of the order of 100 lines laterally. So-called A-lines run actually from each transducer into the tissue under investigation; a so-called B-scan or B-mode image comprises a plane including a plurality of A-lines, thus defining a vertical cross section through the tissue. A B-scan is typically presented as a two-dimensional brightness image. A two-dimensional transducer array may be used to capture perpendicular B-scan images, for example to provide data for a three-dimensional volume.

A captured image is generally built-up by successively capturing data from along each of the A-lines in turn, that is by capturing a column of data centred on each ultrasonic transceiver in turn (although beam steering may be employed). However, when capturing data from a particular line, preferably a set of the transducers is driven, with gradually increasing phase away from the line on which the transducer is centred so as to create an approximately spherical ultrasonic wavefront converging on a focus on the line under investigation. The signals received from the transducers are summed with appropriate amplitude and phases to reconstruct the line data. This provides an RF (radio frequency) output which is usually time-gain compensated (because the amplitude of the received signal decreases with increasing probed depth) before being demodulated, optionally log-weighted and displayed as B-scan. Often the RF data is digitised at some point in the processing chain, for example prior to the demodulation, the remainder of the processing taking place in the digital domain. A pair of analogue-to-digital converters is typically employed to provide in-phase and quadrature digitised signal components so that phase data is available.

At least one-dimensional image data captured by a pulse-echo technique, in particular an ultrasonic imaging system, can be processed to determine deformation (displacement) data. The ultrasonic image data to be processed comprises digitised RF signal data, optionally with pre-processing in the analogue domain. Broadly speaking the demodulated data may be processed by envelope detection and log weighting to provide a B-mode display and/or strain determination may be employed to provide a strain display. The demodulation extracts the amplitude (envelope) and phase information of the RF signal in a conventional manner and the signal is digitised after demodulation so that the processed RF signal comprises a demodulated baseband signal; in other systems the RF signal may be digitised prior to demodulation.

A digitised I and Q (in-phase and quadrature) signal is frequently available in conventional ultrasonic imaging equipment and, conveniently, embodiments of the invention described later may be implemented by processing this signal using a suitably programmed general purpose computer or digital signal processor (DSP) and/or by using dedicated hardware.

Consider the task of estimating the deformation between a pair of RF ultrasound frames acquired pre- and post-deformation, when in general displacement is a continuously varying function of location. Displacement may be estimated by positioning a window over a small section of data in the pre-deformation frame and locating the closest matching window in the post-deformation frame. The displacement estimate is the difference between the pre- and post-deformation window positions.

The window matching approach to deformation estimation is sometimes problematic: pre- and post-deformation windows often match poorly, because deformation may not be negligible on the scale of the individual windows. Thus the post-deformation signals may be warped to increase the correlation between pre- and post-deformation windows, to implement an "adaptive" strain estimator. The simplest adaptive method is to apply a uniform stretch to the post-deformation signal, aiming to reverse part of the signal transformation that has actually taken place. Deformation data from adaptive strain estimators are measurably less noisy than standard displacement estimation, but the improvement is accompanied by a considerable increase in computational cost.

The task of window matching entails adjusting the post-deformation window position in order to find the optimum in a measure of signal similarity. One measure is the correlation coefficient, although similar performance may be obtained from techniques employing alternative measures such as the sum of squared differences (F. Viola and W. F. Walker, "A comparison of the performance of time-delay estimators in medical ultrasound", IEEE Transactions on Ultrasonics, Ferroelectrics, and Frequency Control, 50(4):392-401, April 2003) and the phase of the complex cross-correlation function (X. Chen, M. J. Zohdy, S. Y. Emelianov, and M. O'Donnell, "Lateral speckle tracking using synthetic lateral phase", IEEE Transactions on Ultrasonics, Ferroelectrics, and Frequency Control, 51(5):540-550, May 2004; M. O'Donnell, A. R. Skovoroda, B. M. Shapo, and S. Y. Emelianov, "Internal displacement and strain imaging using ultrasonic speckle tracking", IEEE Transactions on Ultrasonics, Ferroelectrics, and Frequency Control, 41:314-325, May 1994). The estimation procedure is repeated throughout a grid of locations, until the displacement field has been adequately sampled. We have recently noted, however, that window matching approaches can be enhanced: Since finite length windows are used to produce displacement estimates with low noise, the accuracy of the data can be improved by estimating the location at which the displacement estimate is valid. Implicitly assuming that the location is the window centre, results in an "amplitude modulation" artefact with the RF signal amplitude modulating the strain image. For this reason, we call our location estimation technique Amplitude Modulation Correction (AMC), and we have demonstrated that AMC yields better performance at lower computational cost than adaptive strain estimation (J. E. Lindop, G. M. Treece, A. H. Gee, and R. W. Prager, "Estimation of displacement location for enhanced strain imaging", Technical Report CUED/F-INFENG/TR 550, Cambridge University Department of Engineering, March 2006). Further details of AMC can be found in our UK patent application no. 0606125.3 filed on 28 Mar. 2006 and also PCT/GB2007/050158 filed 27 Mar. 2007 hereby incorporated by reference in their entirety.

AMC can be implemented particularly easily in conjunction with phase-based displacement estimators and we have described a new family of highly versatile algorithms which we refer to as Weighted Phase Separation (WPS) in GB 0610172.9 filed 23 May 2006 and in PCT/GB2007/050163, filed 28 Mar. 2007, both hereby incorporated by reference in their entirety.

However, one of the engineering challenges in strain imaging is the development of a suitable clinical interface. Ultrasound clinicians have extensive experience with existing scanning modes including B-mode/greyscale, colour Doppler and power Doppler. Given the highly interactive nature of ultrasound examinations, the established modes have advantages in that clinicians are already well practised in the required scanning technique, they understand the significance of typical images, and they are generally familiar with its uses, benefits and disadvantages. The likelihood of an addition to the ultrasound tool-set gaining clinical favour may be boosted if it can be presented with an interface that: actively fosters the development of a successful scanning technique, by providing either visual or audio feedback; displays data in an intuitively meaningful format; and automatically guards against the presentation of misleading data.

Background prior art can be found in EPO 843 181A, which describes varying the dynamic range and noise rejection level of an ultrasonic image, and in U.S. Pat. No. 6,558, 324 which describes displaying a colour-coded elasticity profile along with a B-mode display in a single, overlaid display.

The aforementioned issues concern how we present information. We may also consider what information to present. This raises at least two further issues. Qualitatively, what type of information can be provided (stiffness, strain, or an alternative compromise)? Quantitatively, how much data should be amalgamated to form each display image? The latter applies to many types of imaging systems, particularly those pertaining to time series data (where persistence may be helpful, whether in a real time display during acquisition or for post-processing) and to volumetric data (where spatial compounding can be applied to reduce noise).

Regarding the type of information, we note that ultrasonic strain imaging falls within a broader set of emerging elasticity imaging techniques. These are all essentially concerned with mechanical properties such as tissue stiffness, of which strain is only an indicator. Strain measurements can be converted into stiffness estimates if the stress field is known, but it is highly unlikely that this can be inferred from static (or quasistatic) deformation data without reducing the resolution and imposing limiting assumptions. Furthermore, such assumptions are unlikely to hold even approximately under in vivo scanning conditions, especially not with freehand scanning. On the other hand, strain images can in themselves sometimes be misleading, because an interpretation of low strain as indicating relatively high stiffness may be erroneous if the stress field varies substantially throughout the tissue. Some types of stress field variation occur repeatedly, and can hence be adjusted for. We will discuss the use of strain normalisation that varies both between images and within every individual image, so as to reduce the ambiguity of strain—we refer to the modified data after non-uniform normalisation as "pseudo-strain".

In practice, an often more severe obstacle in freehand strain imaging is the basic challenge of achieving an acceptable strain estimation signal-to-noise ratio. Although many frames individually produce good images, typically a substantial fraction (and sometimes a majority) of frames may be difficult to interpret because of high estimation noise.

SUMMARY OF THE INVENTION

Broadly we will describe various aspects of a novel interface concept that we have developed to support a wide-ranging clinical trial of ultrasonic strain imaging. The new interface tackles numerous issues, including those mentioned above, to improve the quality of data that clinicians can acquire, and to improve the interpretability of the display. We present results exemplifying all of these aspects in application to real scan data both from in vitro and from in vivo targets.

According to the present invention there is therefore provided a method of displaying strain image data for an imaged object, the method comprising: capturing strain image data defining deformation of said object over an imaged region of said object; determining local image quality data, said local image quality data comprising a measure of the quality of said strain image data varying over said imaged region; and displaying a representation of said strain image data for said imaged region of said object, using said local image quality data to provide a visual indication of the quality of said displayed representation varying over said imaged region or to improve a quality of said displayed representation of said strain image data.

In embodiments determining of the local image quality data comprises processing the strain image data to determine the local image quality data. In embodiments the representation of the strain (elasticity) image data may comprise representation of displacement, or strain, or stiffness of the imaged object in either one, two or three dimensions. In embodiments the local image quality data comprises corresponding one, two or three-dimensional data defining a local precision (or error) in the displacement or strain data. Thus, broadly speaking, associated with the one, two or three-dimensional displacement or strain data there is corresponding one, two or three-dimensional precision or error data.

In some embodiments local image quality data may be derived directly from the original signals. However in preferred embodiments the processing of the strain image data to determine local image quality data comprises determining displacement or strain data over the imaged region and associated error data, normalising the displacement or strain data (over the imaged region) and normalising the error data using a normalisation value derived during the normalising of the displacement or strain data. More particularly the normalising of the displacement or strain data may comprise determining a local (one, two or three-dimensional) normalisation factor for the displacement or strain data and scaling the error data by the square of this local normalisation factor. Thus if the error data represents precision, this precision may be reduced or divided by the square of the local normalisation factor (or equivalently the error increased by the same factor).

A range of techniques may be employed to determine local precision or error data—for example this may comprise a function of a correlation between pre- and post-deformation data windows scaled by a window length. Optionally an additional non-linear transformation may be applied to this using a transformation of the type described the inventors in J. E. Lindop, G. M. Treece, A. H. Gee, and R. W. Prager, Dynamic resolution selection in ultrasonic strain imaging, Technical Report CUED/F-INFENG/TR 566, Cambridge University Department of Engineering, September 2006. Alternatively an error may be calculated from the variance of different phases within a weighted phase separation window technique as previously mentioned. The skilled person will understand, however, that other techniques may also be employed to determine local precision or error data.

In some preferred embodiments the displacement or strain data comprises two (or more) dimensional data and the normalising comprises fitting a tilted or curved surface to this data. For example, stress may be applied to the object or tissue under investigation by motion of the hand of a user holding an ultrasonic probe against the object or tissue (in embodiments involuntary vibration or trembling of the user's hand is sufficient). Such a technique will create greater pressure near the probe than at depth within the tissue and/or may create pressure which is more towards one side or the other of the image. Thus by employing a tilted or curved surface normalisation these effects can be at least partially compensated for, presuming that the object or tissue under investigation does not itself show such a variation. For example without this approach imaged object or tissue can appear to get stiffer with increasing distance from the probe whereas this in fact may be an artefact of the processing.

In some preferred embodiments cumulative displacement or strain data from a plurality of image frames is combined weighted by the local image quality data. The image frames may be either temporal, or spatial (for example 2D slices of a 3D image) or both. Combining the data in this way can result in cumulative displacement or strain data in which the combined result is better than the best data from any single image frame because the weighting in effect picks out the best region(s) of the image frame.

Preferably the local image quality data is also accumulated in a similar way to provide an improved visual indication of the quality of the displayed representation. Most preferably both the displacement or strain data and the local image quality data are accumulated or persisted over multiple image frames.

In embodiments the displaying comprises displaying a representation of the strain image data for the imaged region and, at substantially the same or a similar resolution, a visual indication of the quality of the displayed representation of the strain image data. For example in a pixellated display preferably the local image quality data is calculated on a per-pixel basis. This may then be used to display both the strain image and the local image quality in substantially 1:1 correspondence, for example mapping both into a single colour space for each pixel such as RBG or YUV (as the skilled person will understand such a colour space may include luminance as a parameter). Thus in embodiments both quality and elasticity values are colour coded, in embodiments the quality value (of, say, a pixel) controlling the colour of the strain image (of, say, the pixel).

Thus in embodiments both the representation of the strain image data and the visual quality indication comprise corresponding one, two or three-dimensional data sensor arrays of data. Effectively both the displayed representation and the quality indication are functions of one, two or three-dimensional coordinates specifying a position in the imaged object in one, two or three-dimensions respectively.

In some embodiments the representation of a strain image data of the imaged region of the object comprises a monochrome, for example "black and white" (i.e. grey scale) representation and the visual indication of quality uses one or more colours, for example red for poor quality data and/or green for good quality data. It would be appreciated, however, that potentially one colour (for example, green) may be used to represent quality and two other colours (for example, red and blue) may be employed to represent the strain image data.

It has been found in practice that employing a monochrome, more particularly a grey scale representation for the strain image data appears to facilitate the human eye picking out detail from the image; in this case a colour such as red, can be used to indicate unreliable data.

In other embodiments it has been found helpful to adjust the brightness of the displayed representation of the strain image data according to image quality, in particular reducing the brightness when the quality of the displayed representation is reduced. With this approach unreliable data can be given a low or zero brightness so that it is effectively blanked from the display. This again has been found helpful in practice.

In a related aspect the invention provides a method of displaying strain image data for an imaged object, the method comprising: capturing strain image data defining deformation of said object over an imaged region of said object; processing said strain image data to determine local image quality data, said local image quality data comprising a measure of the quality of said strain image data varying over said imaged region; and displaying a representation of said strain image data for said imaged region of said object; wherein said capturing comprises capturing data for a plurality of image frames; and wherein said displaying comprises determining cumulative displacement or strain data for said imaged region of said object over a plurality of said image frames weighted by said local image quality data.

In embodiments variation of the local image quality over the image region is also displayed, preferably in combination with the strain data, for example mapped into a common colour space (for example RBG, YUV or the like). In embodiments the local image quality data displayed is derived from, for example accumulated, averaged or persisted over, multiple image frames.

The invention further provides apparatus for implementing the above-described aspects and embodiments of the invention for implementing the above-described aspects and embodiments of the invention, in particular including a processor, data memory, and program memory storing instructions for controlling the processor to implement a method according to an aspect of the invention as set out above.

Such apparatus may, for example, be incorporated into or associated with an ultrasonic, MRI (magnetic resonance imaging), CT (computer tomography) or other, in particular medical imaging system.

The skilled person will understand that although some preferred embodiments of the techniques are described with reference to ultrasonic data processing, the techniques may also be employed with strain image data captured using other techniques such as, potentially, magnetic resonance imaging and computer tomography.

The invention further provides processor control code to implement the above-described methods, for example on a general purpose computer system or on a digital signal processor (DSP). The code may be provided on a carrier such as a disk, CD- or DVD-ROM, programmed memory such as read-only memory (Firmware), or on a data carrier such as an optical or electrical signal carrier. Code (and/or data) to implement embodiments of the invention may comprise source, object or executable code in a conventional programming language (interpreted or compiled) such as C, or assembly code, code for setting up or controlling an ASIC (Application Specific Integrated Circuit) or FPGA (Field Programmable Gate Array), or code for a hardware description language such as Verilog (Trade Mark) or VHDL (Very high speed integrated circuit Hardware Description Language), the latter because embodiments of the method may be implemented in dedicated hardware. As the skilled person will appreciate such code and/or data may be distributed between a plurality of coupled components in communication with one another.

Features of the above described aspects and embodiments of the invention may be combined.

BRIEF DESCRIPTION OF THE DRAWINGS

These and other aspects of the invention will now be further described, by way of example only, with reference to the accompanying figures in which.

DETAILED DESCRIPTION OF PREFERRED EMBODIMENTS

Broadly, we will describe an interface for freehand strain imaging, which has been designed to support clinical trials investigating the potential of ultrasonic strain imaging for diagnostic purposes across a broad range of target pathologies. The aim with this interface is to make scanning easier, and to help clinicians learn the necessary scanning technique quickly, by providing real time feedback indicating the quality of the strain data as they are produced. The images are also easier to interpret, because data at unacceptably low signal-to-noise ratios do not reach the display. The main components of the interface are novel normalisation, persistence and display methods. These not only present data in a more meaningful format, but the level of noise in the displayed images may actually be reduced compared to other methods that use the same strain estimates with the same level of persistence.

Figure 1:
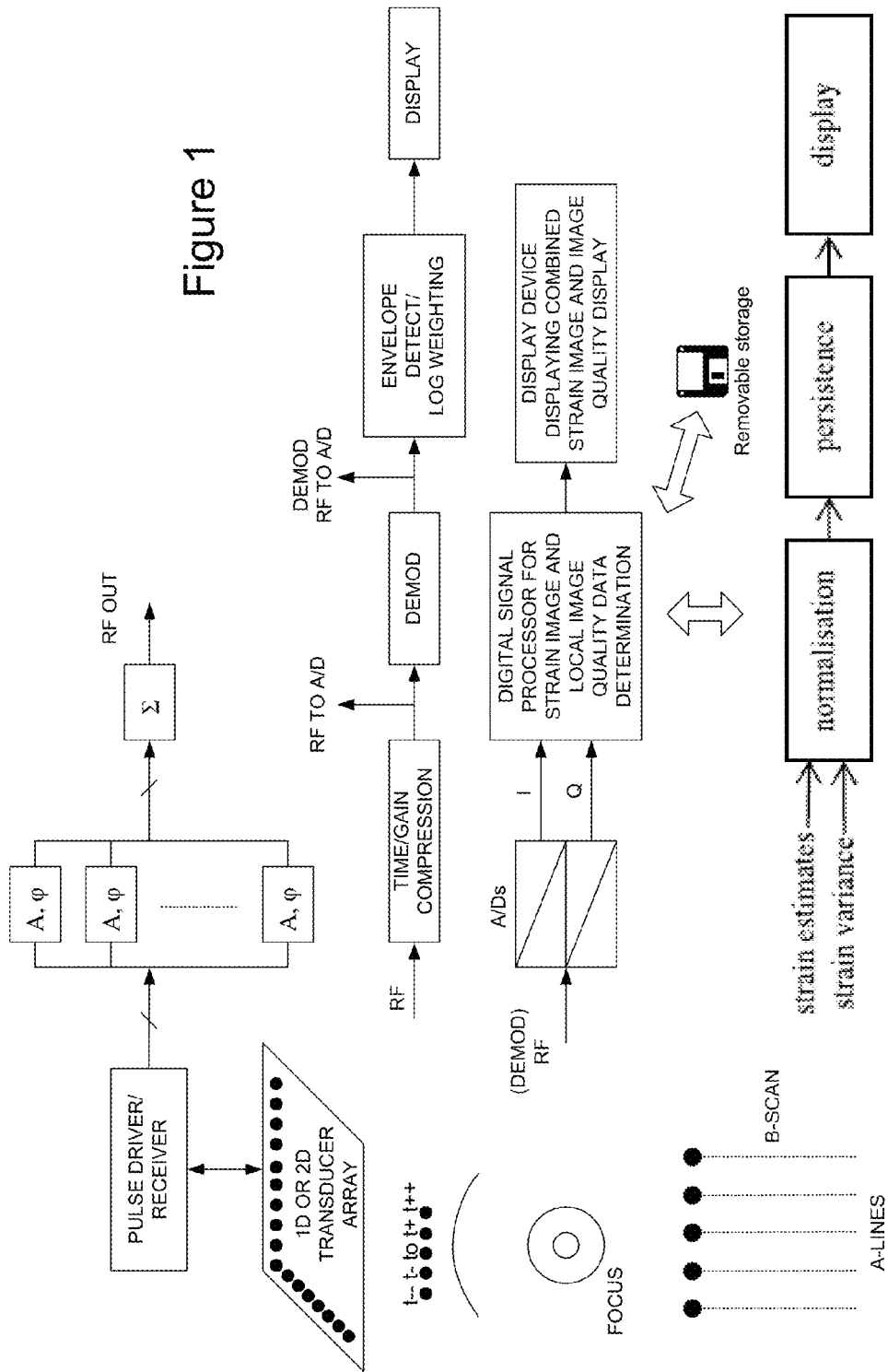
FIG. 1 shows a block diagram of an ultrasonic imaging system configured to implement an embodiment of the invention and including a flow diagram for implementation by the system illustrating conversion of strain estimate and strain variance data into a displayed representation of this data together with a visual indication of the quality of the displayed representation varying over the imaged region.

FIG. 1 shows an outline block diagram of an ultrasonic imaging system configured to implement an embodiment of the invention. This merely illustrates one example of an imaging system in the context of which embodiments of the invention may operate, to assist with understanding of the described embodiments. The skilled person will understand that there are many other types of ultrasonic (and other) imaging systems with which embodiments of the invention may be employed.

The interface concept that we outline here is applicable to many imaging systems, including any static or quasistatic strain imaging system, although the details of its implementation may vary. We provide illustrations based on an example embodiment, in which the displacement tracking is by Weighted Phase Separation [J. E. Lindop, G. M. Treece, A. H. Gee, and R. W. Prager. Phase-based ultrasonic deformation estimation. Technical Report CUED/F-INFENG/TR555, Cambridge University Department of Engineering, May 2006] with Amplitude Modulation Correction and strain estimation is by piecewise-linear least squares regression. This offers a good demonstration, not primarily because of its competitive estimation accuracy, but more importantly because it has already been analysed and tested rigorously, resulting in a promising method for predicting the strain estimation variance [J. E. Lindop, G. M. Treece, A. H. Gee, and R. W. Prager, Dynamic resolution selection in ultrasonic strain imaging. Technical Report CUED/F-INFENG/TR 566, Cambridge University Department of Engineering, September 2006; J. E. Lindop, G. M. Treece, A. H. Gee and R. W. Prager. Dynamic resolution selection in ultrasonic strain imaging. To appear in Acoustical Imaging, Volume 29, I. Akiyama (editor), Springer 2008]. Nonetheless, the focus is a general interface concept for ultrasonic strain imaging, which is likely to be particularly valuable in conjunction with freehand scanning. The interface concept is in principle applicable to any strain imaging system, almost regardless of the approach taken in the earlier stages of signal processing. We begin by providing an overview of the interface as a whole, followed by a brief discussion of predicting estimation precision, and descriptions of each of the three subsequent stages of processing in the interface—normalisation, persistence and display (see FIG. 1).

Interface Concept

Strain image quality varies substantially depending on the sonographer's scanning technique, physiological motion in the tissue, and changes in the analytical parameters for converting RF ultrasound data into strain data. In order to produce consistently meaningful images, these parameters need to be controlled locally so as to adjust for different conditions during the scan. [J. E. Lindop, G. M. Treece, A. H. Gee and R. W. Prager. Dynamic resolution selection on in ultrasonic strain imaging. Technical Report CUED/F-INFENG/TR 566, Cambridge University Department of Engineering, September 2006; and J. E. Lindop, G. M. Treece, A. H. Gee, and R. W. Prager. Dynamic resolution selection in ultrasonic strain imaging. To appear in Acoustical Imaging, Volume 29, I. Akiyama (editor), Springer 2008] describe such a system. However, parameter adjustment alone cannot overcome all of the difficulties in practical strain imaging. For a start, at some stage it becomes impossible to produce meaningful deformation data from frames that are extremely weakly correlated. An adequate minimum level of correlation may not always arise, depending on the scanning technique, and with a very poor technique it may not even occur often. Even in the majority of frames where a uniform estimation signal-to-noise ratio can be achieved by adjusting the resolution settings, it is desirable to improve the quality of the recorded ultrasound data, so as to achieve the highest possible resolving power. The best data may arise when relatively substantial deformation occurs (i.e., typically a large fraction of 1%, sometimes lower or higher depending on the target) accompanied by relatively little decorrelation. The acquisition of good data therefore depends on the combined properties of the scanning technique and the tissue.

Figure 2:
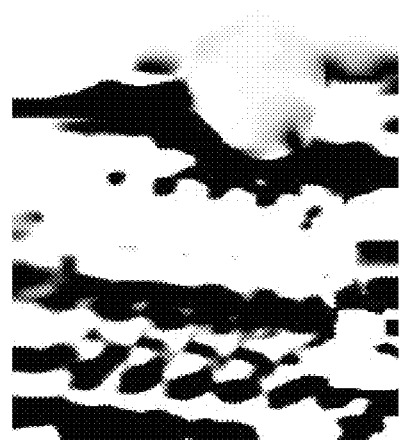
FIG. 2 shows typical images during freehand scanning without the new interface. (a) The strain display is filled with noise before the probe comes into contact with tissue, although (b) the B-mode image shows that there is obviously nothing to be seen. However, the images are actually more difficult to interpret when the probe is in contact with the tissue. For example, while scanning a thyroid (c) the strain display contains a mixture of good estimates alongside regions of noise, without an obvious boundary. This is unsurprising given that (d) the B-scan has regions with a high signal-to-noise ratio alongside other regions where there is simply no signal, and a region of severe decorrelation around the artery caused by blood flow and pulsatile motion.
Figure 2:
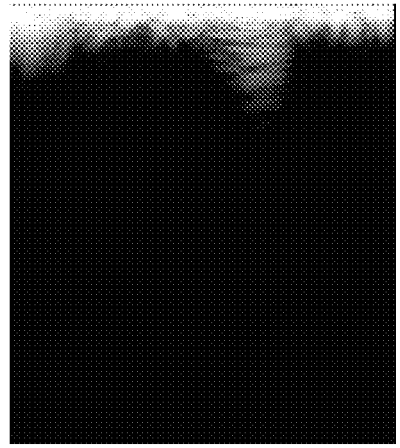
Figure 2:
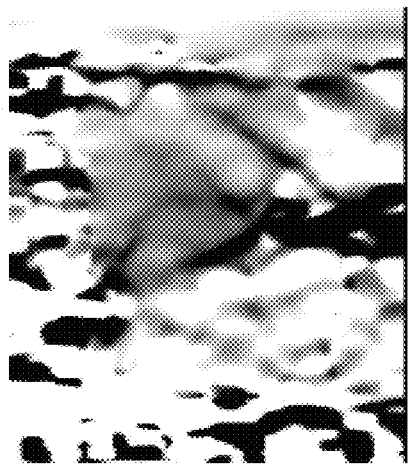
Figure 2:
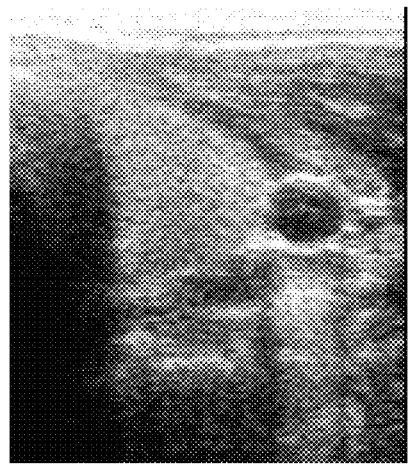

Strain imaging with a typical interface requires a high level of expertise, in terms both of scanning technique and of image interpretation. The examples in FIG. 2 illustrate some difficulties. The use of a side-by-side display with the B-scan next to the strain image, is easier to match up strain data with features of interest that have already been identified in the B-scan. It also means that in cases where there may be little or no data, owing to an absence of coupling to the tissue, as for example in FIG. 2*a-b*, then the sonographer knows to ignore the strain display. Image interpretation may nonetheless be rather difficult when the coupling is good, as for example in FIG. 2*c-d*, because many scanning targets are unlikely to give rise to signals suitable for strain imaging throughout the entire image.

Each strain image may be overlaid on the B-scan as a "colour wash", where colour indicates strain and brightness is partly determined by the ultrasound signal amplitude. In so far as ultrasound signal amplitude correlates with the accuracy of strain estimates, this goes some way to indicating the quality of the strain data. It only helps to a limited extent, however, since signal amplitude is a very weak indicator of overall decorrelation. While a complete absence of signal certainly would mean that strain estimates were dominated by noise, it is often the case that strain estimates from regions with medium signal amplitude are less noisy than other estimates where the signal is stronger. Furthermore, the blend of strain with B-mode data could actually make insightful image interpretation more difficult, by mixing strain data with fine features of B-scans such as the speckle pattern, that are in fact not generally related to tissue stiffness.

Therefore, we use accurate indicators of the precision of each strain estimate, which influences our use of these estimates age downstream including the display. An appropriate strain normalisation may be calculated by fitting a suitably constrained surface to the entire set of displacement data in each frame, possibly by the method of precision-weighted least squares. Normalisation can be applied both to the strain data and also to the associated precision data, producing a new array of pseudo-strain data with updated precision values. Having produced a single frame of pseudo-strain, the signal-to-noise ratio may be boosted by applying some form of compounding or persistence, which may again be weighted according to precision, from which the output would be a set of persisted pseudo-strain values and appropriately updated precisions. Finally, the display scheme can be tailored to indicate both strain and precision data on a two-dimensional (2D) scale represented by a 2D colour map.

Predicting Estimation Precision

Our system exploits the availability of useful predictions of strain (and/or displacement) estimation precision. The means of achieving these predictions is not critical, although the advantages of our concept are likely to be greatest if the precision predictions are highly accurate. The prediction method employed to produce results in this report is based on the work reported in J. E. Lindop, G. M. Treece, A. H. Gee, and R. W. Prager. Dynamic resolution selection in ultrasonic strain imaging. Technical Report CUED/F-INFENG/TR 566, Cambridge University Department of Engineering, September 2006.

To summarise, precision is the reciprocal of variance or mean squared error. Displacement precision can be predicted by evaluating $Tc/(1-c)$, where c is the correlation coefficient between pre- and post-deformation data in the displacement estimation window and T is the window length. The precision of each displacement estimate is the reciprocal of its variance. In each least squares kernel, the overall strain estimation variance can be predicted by evaluating an average of the displacement variances weighted by the square of the distance from the kernel centre, and dividing through by the sum of squared distances. A more accurate estimate can be produced by applying a more complicated formula that accounts for the correlations between nearby errors [J. E. Lindop, G. M. Treece, A. H. Gee, and R. W. Prager. Dynamic resolution selection in ultrasonic strain imaging. Technical Report (CUED/F-INFENG/TR 566, Cambridge University Department of Engineering, September 2006]. This was not applied in the results that we present here—although it might bring a slight improvement in some cases—because it is less important when we only consider fixed analytical parameters, and we only require predictions of relative (rather than absolute) precision. The results that we present are therefore based on the following approximation for strain estimation precision, $W_A$:

$$W_A(x,y) = \frac{\left(\sum_i y_i^2\right)^2}{\sum_j y_j^2 (1-c_j)/(T_j c_j)}$$

where the sums are over displacement data in the least squares regression kernel centred on pixel $(x,y)$, and y denotes distance from the centre of the kernel along the direction in which strain is being estimated.

Normalisation

Careful design of the normalisation strategy may contribute to valuable improvements in the quality of the strain images, particularly if the scanning procedure is real time and/or freehand. (See, for example, J. E Lindop, G. M. Treece, A. H. Gee, and R. W. Prager. Frame filtering for improved freehand 3D US elastography. In *Ultrasonic Measurement and Imaging of Tissue Elasticity*, page 74 Austin, Tex., October 2005; and J. E. Lindop, G. M. Treece, A. H. Gee, and R. W. Prager. 3D elastography using freehand ultrasound. *Ultrasound in Medicine and Biology*, 32 (4): 529-545, April 2006). The basic problem of finding an appropriate strain scale for each image can be solved robustly by fitting a plane to the entire set of displacement estimates, $\{d(x,y)\}$— this is performed in our examples by the method of precision-weighted least squares—thereby determining an "average" strain. The equation of the fitted plane would be as follows:

$$\hat{d}(x,y)=\alpha+\hat{s}y$$

The strain estimates can be scaled so that the dynamic range in the display ranges from zero up to a fixed multiple of the average strain, $\hat{s}$.

In the new interface, we also introduce extensions of this approach, by fitting other parametric surfaces to the set of displacement estimates. For instance, we can adjust for the reduced stress at greater depths away from the probe, as the stress spreads out into the surrounding tissue:

$$\hat{d}(x,y)=\alpha_0+\alpha_1 x+\beta_1 y+\beta_2 y^2 \tag{3a}$$

$$\hat{s}(x,y)=+\beta_1+2\beta_2 y \tag{3b}$$

It is therefore more appropriate to refer to $\hat{s}(x,y)$ as a "normalisation" strain, rather than an average, since it is a function of image position. Having found the parameters $\beta_1$ and $\beta_2$—which we again evaluate in our examples by weighted least squares regression—we can divide through by the local value of $\hat{s}(x,y)$ in order to normalise each strain estimate.

A further extension can be made to adjust for the possibility that the probe may rotate during the scan, resulting in stress variation over the lateral direction.

$$\hat{d}(x,y)=\alpha_0+\alpha_1 x+\beta_1 y(1+\beta_2 y)(1+\beta_3 x) \tag{4a}$$

$$\hat{s}(x,y)=\beta_1(1+2\beta_2 y)(1+\beta_3 x) \tag{4b}$$

Again, the parameters $\beta_1$, $\beta_2$ and $\beta_3$ can be found by weighted least squares regression, or a suitable alternative, thereby defining the normalisation strain at every position throughout the image.

It is worth noting that all of our normalisations can be applied both to the strain estimates and also to the associated precision values. Since normalisation applies a scaling of $1/\hat{s}(x,y)$ both to good measurements and to errors, it may also be appropriate to scale the precision (reciprocal of mean squared error). We scale precision by $\hat{s}(x,y)^2$ in the present example embodiment. If we denote pre-normalisation strain estimates and post-normalisation pseudo-strain by $s_A$ and $s_B$, with $W_A$ and $W_B$ respectively denoting the pre- and post-normalisation precisions, then $$s_B(x,y)=s_A(x,y)/\hat{s}(x,y) \tag{5a}$$

$$W_B(x,y)=W_A(x,y)\times \hat{s}(x,y)^2 \tag{5b}$$

Appropriate normalisation of precision is strongly preferable, since the practical effect of the combined normalisation is to place each individual strain estimate on a broad scale of possible interpretations, depending on its relative properties in the context of the entire frame of scan data. Depending on the value of $\hat{s}(x,y)$, the normalisation of any single data pair consisting of one strain estimate and its precision value is normalised within a range spanning (1) relatively low pseudo-strain at relatively high precision, through to (2) relatively high pseudo-strain at relatively low precision. The form of normalisation therefore potentially influences not only the type of image, but also its accuracy.

It bears noting that the main computational expense in normalisation is the fitting of a parametric (or suitably constrained non-parametric) displacement surface, but this in itself is typically a negligible cost on widely available GHz processors in the context of frame rates below 1000 Hz. Computational efficiency is one of the main factors behind the selection of the particular parametric forms that we provide as examples. However, Equations 2 and 5 imply linear variation with depth in the normalisation strain. This may usually be a good approximation, but it leaves open the possibility that the sign of the normalisation strain could invert at some depth within the image. If this were a reasonable form of normalisation, it would imply that at some depth the direction of the stress field inverts, i.e., that a compression at the surface causes extension at greater depth within the tissue. This is unrealistic, but it can be prevented, for example by constraining the fitted surface to avoid the strain crossing zero within the image depth (as in the images presented in this report) or alternatively data below the zero crossing of the normalisation strain can be treated as uninformative, by setting the precision to zero.

The normalisation surface might ideally reflect exponential variation with depth, but a least squares fit would then incur much greater computational cost. Our demonstration employs the normalisation surfaces outlined above for efficiency, not precluding the possibility that other parametric or constrained non-parametric forms may be found in the future, offering better performance at reasonable cost.

Figure 3:
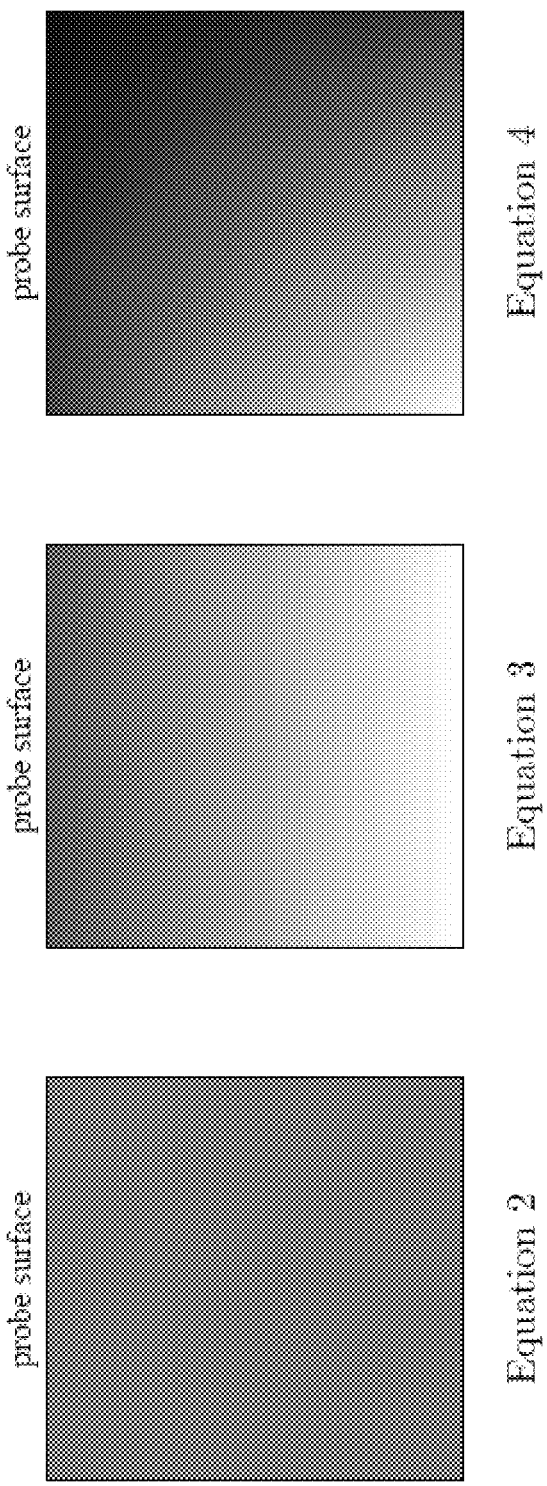
FIG. 3 shows an illustration of the types of strain fields that may produce uniform pseudo-strain fields—indicating homogeneous stiffness—with each of our normalisation options. The first option only adjusts for stress variation on the level of the whole image, while the second adjusts for lower stress away from the probe surface, and the third also adjusts for uneven probe pressure.

FIG. 3 illustrates the strain fields that are implied by each of the normalisation scheme examples, or equivalently the stress fields that might produce such a field in homogeneous material. The key with the normalisation is to fit a suitably constrained surface, that with high probability corrects for artifacts associated with the uneven distribution of stress within the tissue, without removing information that has arisen owing to genuine differences in stiffness.

It is possible—but unlikely—that there may be tissue in which stiffness in fact varies with the reciprocal of depth, and the application of a uniform stress field may also be possible, in which case normalisation using Equation 2 or Equation 5 would remove real stiffness data from the display. The frequency with which this sort of ambiguity arises will depend on the scanning target, so it may be that different normalisation surfaces are required for different clinical applications.

Persistence or Compounding

Persistence refers to time-averaging of image data, while compounding refers to averaging more generally. In general, our preferred approach is to perform averaging after normalisation in the form of a precision-weighted average on a per-pixel basis. We also sum the precision values, since it can be shown that the overall precision of a (correctly) precision-weighted average of data with uncorrelated errors is equal to the sum of precisions.

In the context of producing a real time interface for freehand imaging with two spatial image dimensions, we perform this averaging as a form of persistence on the arrival of each new frame, f. The values that persist in pre-display buffers at pixel (x,y) are a precision-weighted sum, $S(x,y,f)$, and the sum of precisions, $\Omega(x,y,f)$. These buffers are updated on the arrival of each new frame, providing new pseudo-strain data, $s_B(x,y,f)$, and new precisions, $W_8(x,y,f)$.

$$S(x,y,f)=\gamma S(x,y,f-1)+W_B(x,y,f)s_B(x,y,f) \quad (6a)$$

$$\Omega(x,y,f)=\gamma\Omega(x,y,f-1)+W_B(x,y,f) \quad (6b)$$

Here $\gamma$ is a number between 0 and 1 that determines the level of persistence. Each persisted pseudo-strain is given by $S(x,y,f)/\Omega(x,y,f)$, accompanied by a precision (quality) value for the display, $\Omega(x,y,f)$. In preferred embodiments, sonographers using our interface should be presented with a meaningful display, representing data quality as well as strain, in which the appearance of the images would be determined jointly by both quantities.

It should be noted that, although in this report we demonstrate persistence applied at the level of pseudo-strain, it is also possible to persist (uniformly or non-uniformly) normalised displacement and displacement precision data. Displacement normalisation requires fitting the same normalisation surfaces as before to determine $\hat{d}(x,y)$ and $\hat{s}(x,y)$. The normalisation calculation then comprises subtracting $[\hat{d}(x,y)-\hat{s}(x,y)y]$ from the displacements before scaling by $1/\hat{s}(x,y)$, while the precision is again scaled by $\hat{s}(x,y)^2$. The persisted, normalised displacement and associated precision arrays must then be converted to arrays of pseudo-strain and pseudo-strain precision just prior to display. In some systems this variation may yield better results.

Note also that alternative forms of persistence or compounding can typically be achieved by simple variations on the particular persistence method described above. For example, when volumetric data is acquired on a per-volume basis, persistence can be applied easily to pseudo-strain or normalised displacement at the voxel level, for example by modifying Equation 4 so that every quantity is indexed over four dimensions, i.e., (x,y,z,f). More generally, it is also possible to apply compounding over all four of these dimensions for noise suppression in a form other than persistence, for example by applying a one-, two-, three- or four-dimensional smoothing kernel, which should preferably incorporate the same precision-based weightings as before.

Display

Returning to FIG. 2, an advantage of traditional ultrasound imaging is that signal intensity displays automatically tend to show the most data where the signal is strong, and they show less data where the signal is weak (the image turns black). Similarly, one of our options in pseudo-strain imaging is to control image luminance or intensity based on the precision data, and to use changes in colour (preferably independently of intensity/luminance) to indicate strain. Regarding the colour scheme, our options include the use of a wide range of saturated colours, producing the effect of a contour display but for the present demonstration we favour a dichromatic scale, which is qualitatively closer to traditional intensity-based displays, and which may avoid distorting the features that are perceived to appear in each image. Aiming for maximum colour variation across the scale, in the example embodiment we use green and magenta at the extremes, varying from strong green (high strain/soft) through grey (medium strain/medium stiffness) to magenta (low strain/stiff). Since we perceive different colours with different sensitivity, colour variation at a fixed intensity is achieved following the convention of holding constant the value of while the precision is again scaled by $\hat{s}(x,y)^2$.59×(green pixel value)+30×(red pixel value)+11×(blue pixel value).

Figure 4:
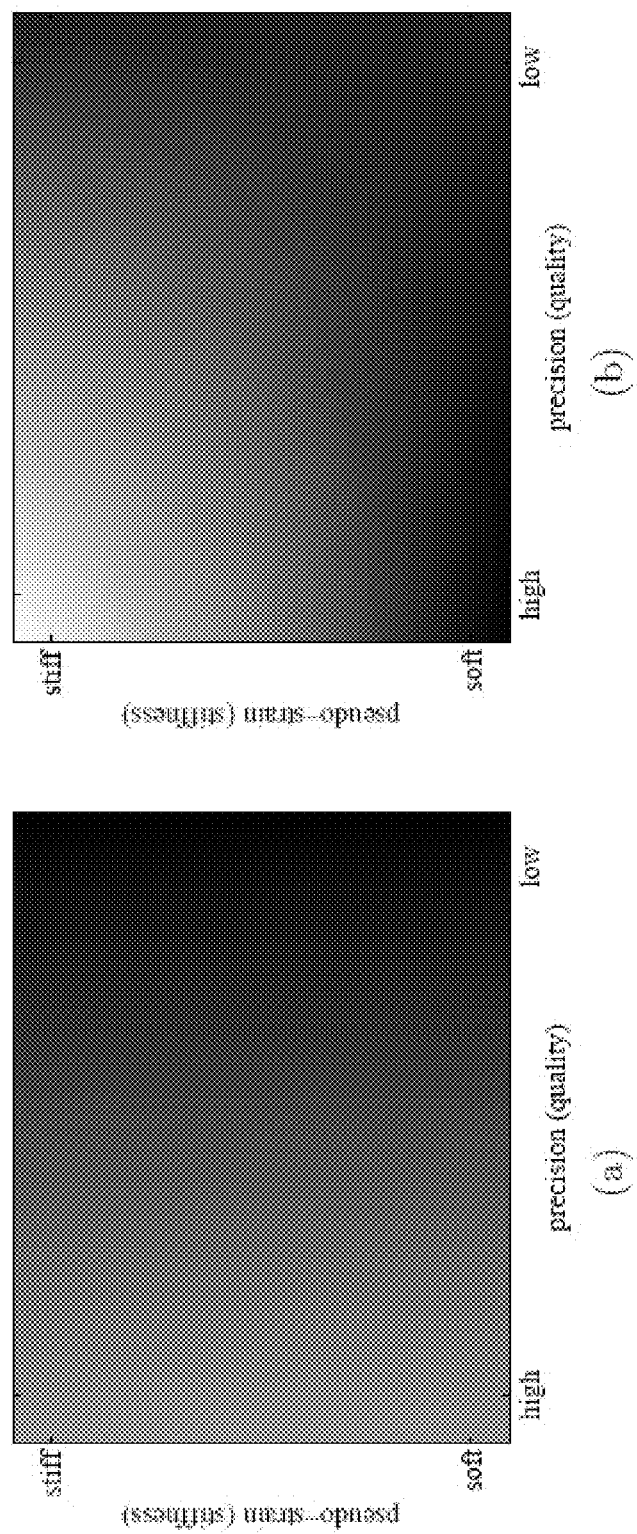
FIG. 4 shows two examples of 2D colour maps. (a) Green through to pink/magenta provides the strain scale, while pixel intensity indicates the data quality within a range from a lower threshold—below which everything appears black—up to a maximum threshold—above which colours are displayed with the maximum intensity. (b) The strain scale is based on intensity variation between black and white, which blends with dull red when the precision is low.

The overall colour map, considering both strain and precision, is illustrated in FIG. 4.

There are likely to be an array of both advantages and disadvantages associated with representing strain with colour instead of intensity, since image features encoded in these two alternative ways are processed with different accuracy and at different speeds by the human visual system. We therefore also test a 2D colour map in which strain is indicated by intensity and a colour (red in our example) is introduced to indicate precision. We include this in FIG. 4 and in our results to provide a comparison. In any event, our aim in relation to displays is simply to demonstrate that a 2D colour map can be used effectively to depict strain and precision data simultaneously.

Note that in the results section we demonstrate 2D colour maps that are encoded with eight bits per pixel. This is usually sufficient to produce good images, because distinctions within the dark and red regions of the colour maps are less perceptible, so these regions can be encoded at low precision. However, 16-bit encoding might be preferable if this type of interface came into widespread clinical use, since the appearance of the display images would then be marginally smoother.

Results

Figure 5:
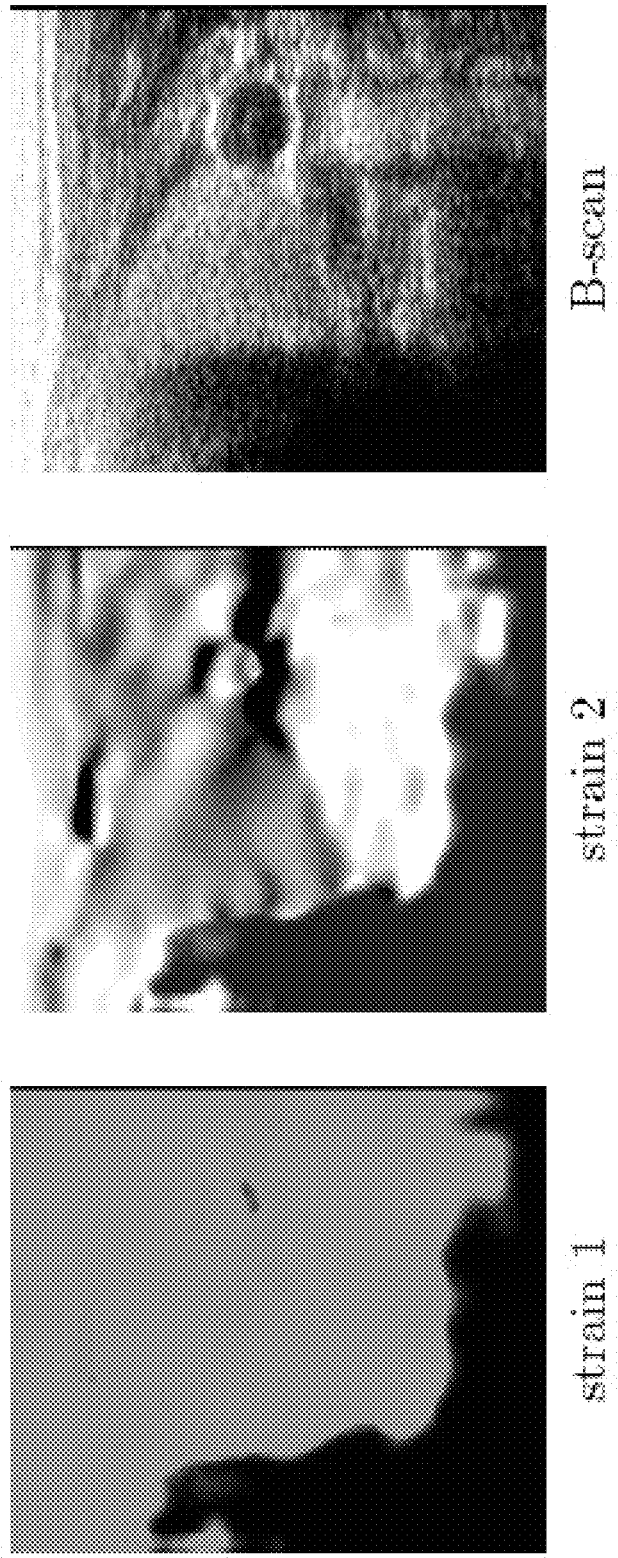
FIG. 5 shows thyroid images using the full interface.

By applying our full interface scheme to the scan shown earlier in FIG. 2, we produce a substantially better image in FIG. 5, employing the combination of intelligent normalisation, persistence and display. Precision-weighted persistence gives rise to good strain estimates throughout most of the image, and the poor precision of estimates in the shadowed regions is clearly indicated by both of the 2D colour maps. This scan was undertaken freehand using the 5-8 MHz 7L3-V probe of the Terason (http://www.terason.com) laptop-based ultrasound machine, fuming Stradwin (http://mi.eng.cam.

ac.uk/rwp/stradwin) freehand 3D ultrasound software. The remainder of this section provides further illustrations from scanning of phantoms, highlighting the properties of each component in our interface, and the interactions between them.

Figure 6:
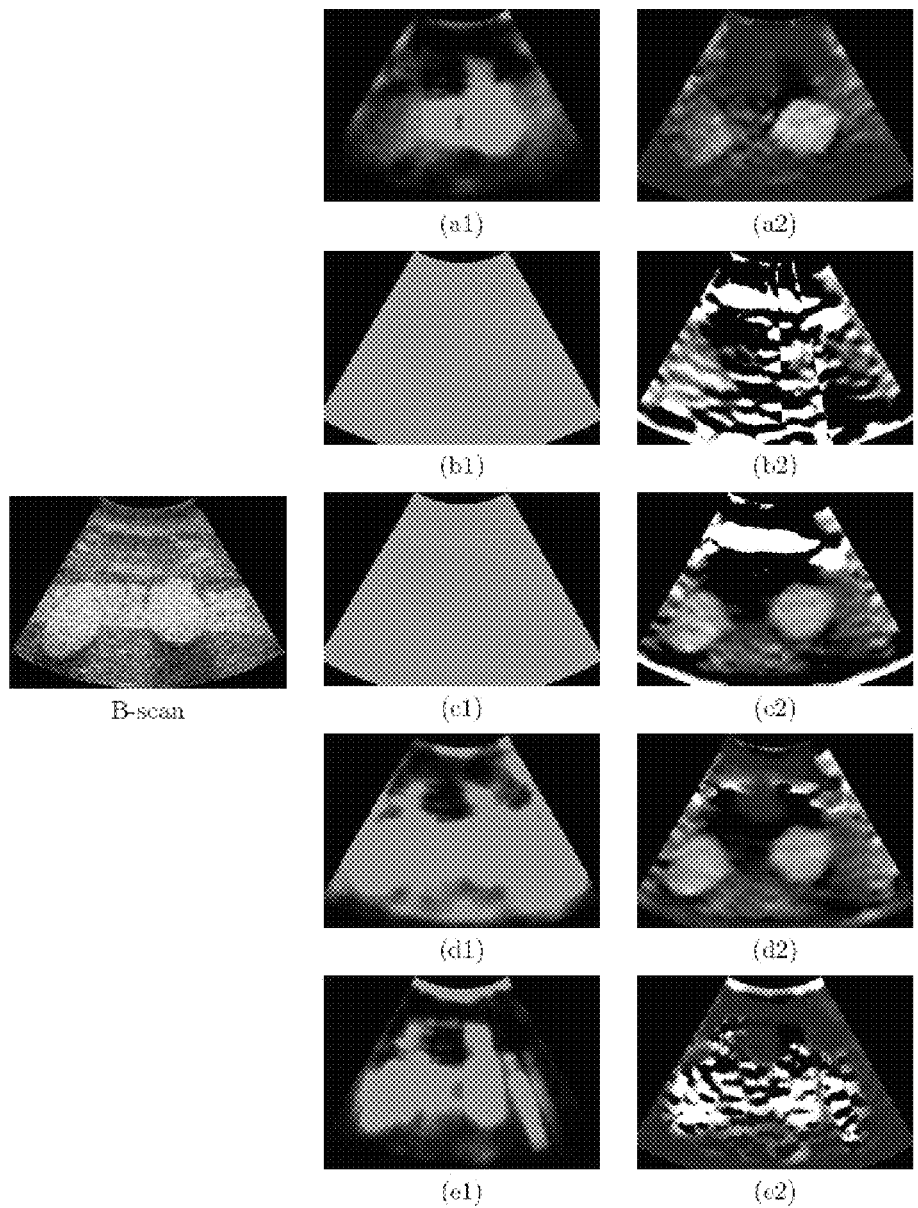
FIG. 6 shows an example of alternative persistence methods in the strain images. (a) Best individual image without persistence: Individual frames produce a mixture of good and bad image regions, which register different levels of precision. (b) Unweighted frame averaging: The unweighted average of an image sequence is noisier than many of the individual frames. (c) Precision-weighted frame averaging: A sequential average weighted by each frame's mean precision significantly reduces the level of noise. (d) Pixel-level precision-weighted persistence: Performing the average with a different weight for every pixel further reduces the level of noise, but only slightly in this example. Its main advantage in this case is the retention of pixel-level persistence data, hence the remaining poor data can be hidden. (e) Less robust displacement tracking: This image has the same persistence, but displacement tracking is by the fragile method of Persistence is more effective in conjunction with robust displacement tracking algorithms.

FIG. 6 illustrates the effect of persistence, using images from an inhomogeneous gelatin phantom with stiff inclusions at a depth of 7 cm, scanned using the convex 2-5 MHz 4C2-A Terason probe. These images are normalised using Equation 5. Individual strain images usually produce some regions of good strain estimates, alongside other regions with lower precision. Unweighted frame averaging as in FIG. 6b might eventually converge on a good image, but for short integration times it is usually less accurate than some of the best individual images. The advantage of persistence, as in FIG. 6c-d, is that it makes efficient use of the data, so better strain images are produced easily, with larger regions of good data and generally less noise. In some scans, as here, the use of an image-wide weighting is sufficient to cut out most of the noise, although pixel-level weightings generally give better results. The other advantage of pixel-level weightings is that a precision value is retained by each pixel in the persisted image, so it is still possible to indicate the data quality using a 2D colour map. However, we include an image produced using a less robust displacement tracking method in FIG. 6e, in which the best form of persistence has been employed. This shows that persistence is far more effective if the rate of severe outliers can be kept to a minimum, because estimates of the precision of gross outlier errors tend to be too high. Persistence is highly effective in conjunction with our phase-based algorithms, because of the implicit continuity constraint that was introduced by the advanced iteration seeding strategies described in J. E. Lindop, G. M. Treece, A. H. Gee, and R. W. Prager. Phase-based ultrasonic deformation estimation. Technical Report CUED/F-INFENG/TR 555, Cambridge University Department of Engineering, May 2006; and G. Treece, J. E. Lindop, A. H. Gee, and R. W. Prager. Efficient elimination of dropouts in displacement tracking. In *Ultrasonic Measurement and Imaging of Tissue Elasticity*, page 68, Snowbird, Utah, October 2006. This issue also affects exhaustive searching based on correlation coefficient or SAD, where in both cases the imposition of continuity constraints—whether explicitly or implicitly—substantially reduces the rate of outlier errors.

Figure 7:
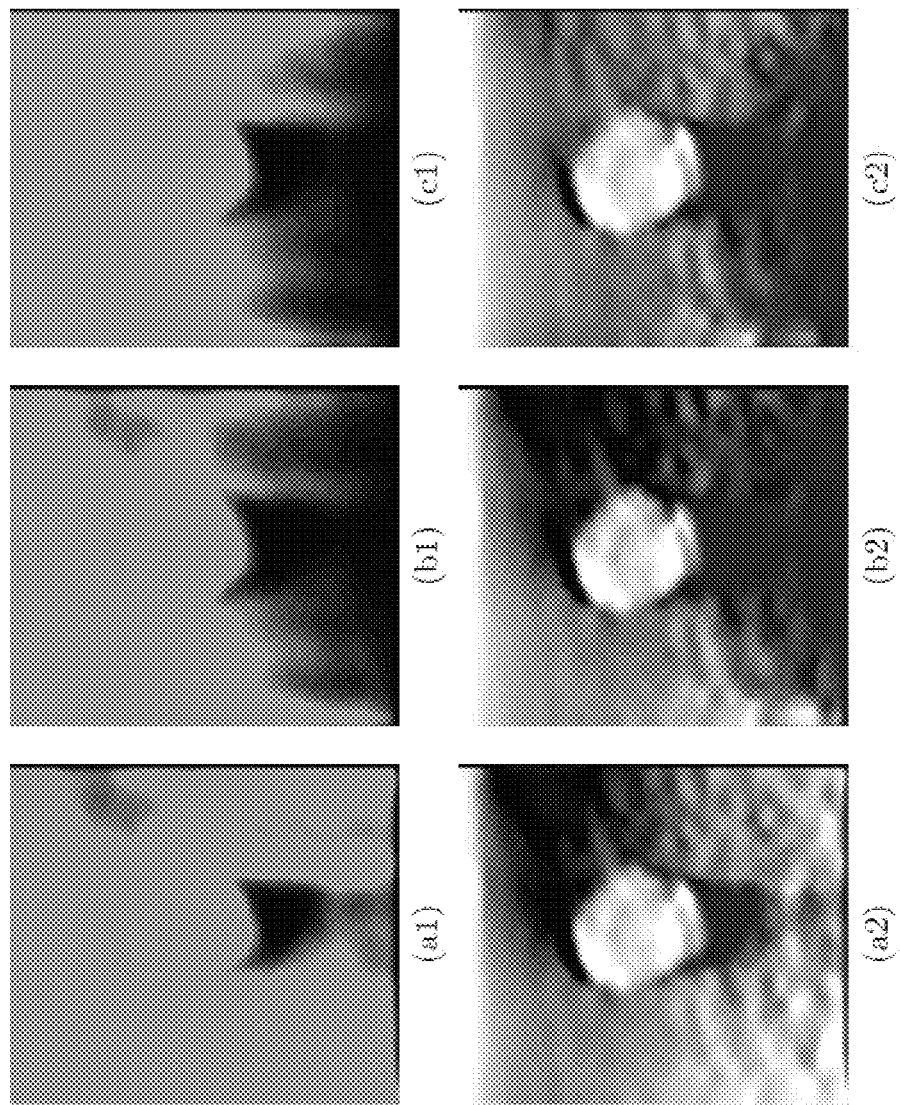
FIG. 7 shows a comparison of normalisation applied to a single individual frame. The normalisation surface is based on (a) Equation 2, (b) Equation 2 and (c) Equation 5.

The next example is from freehand scanning of a breast biopsy phantom (Computerised Imaging Reference Systems, Inc. (http://www.cirsinc.com) Model 052) using the linear array 5-8 MHz Terason probe. The data quality in this case is less dependent on maintaining even probe pressure, because speckle tracking near to the surface is subject to less motion decorrelation, even if the probe does rotate substantially. However, this means that a wider range of motion types register high precision values, which actually makes correct normalisation more important than in the example of FIG. 6. A single frame of strain data with relatively even compression is illustrated in FIG. 7, exhibiting two noteworthy features. The uniform normalisation in FIG. 7a gives the impression of there being stiffer material towards the bottom of the image, where the stress disperses into the surrounding material. The images in FIG. 7b-c are better because the region with lower stress registers instead as having similar pseudo-strain at a lower signal-to-noise ratio, resulting in larger hidden regions. It is also clear from the image that the probe was slightly rotated, so that greater pressure was applied on the right hand side. This gives an appearance of soft material on the right of the image in FIG. 7a-b, including a particularly soft region with low precision data. The background material correctly appears more uniform when we apply the more sophisticated normalisation in FIG. 7c, which not only produces a more uniform appearance in the top right of the image, but the data now register an acceptable level of precision.

Figure 8:
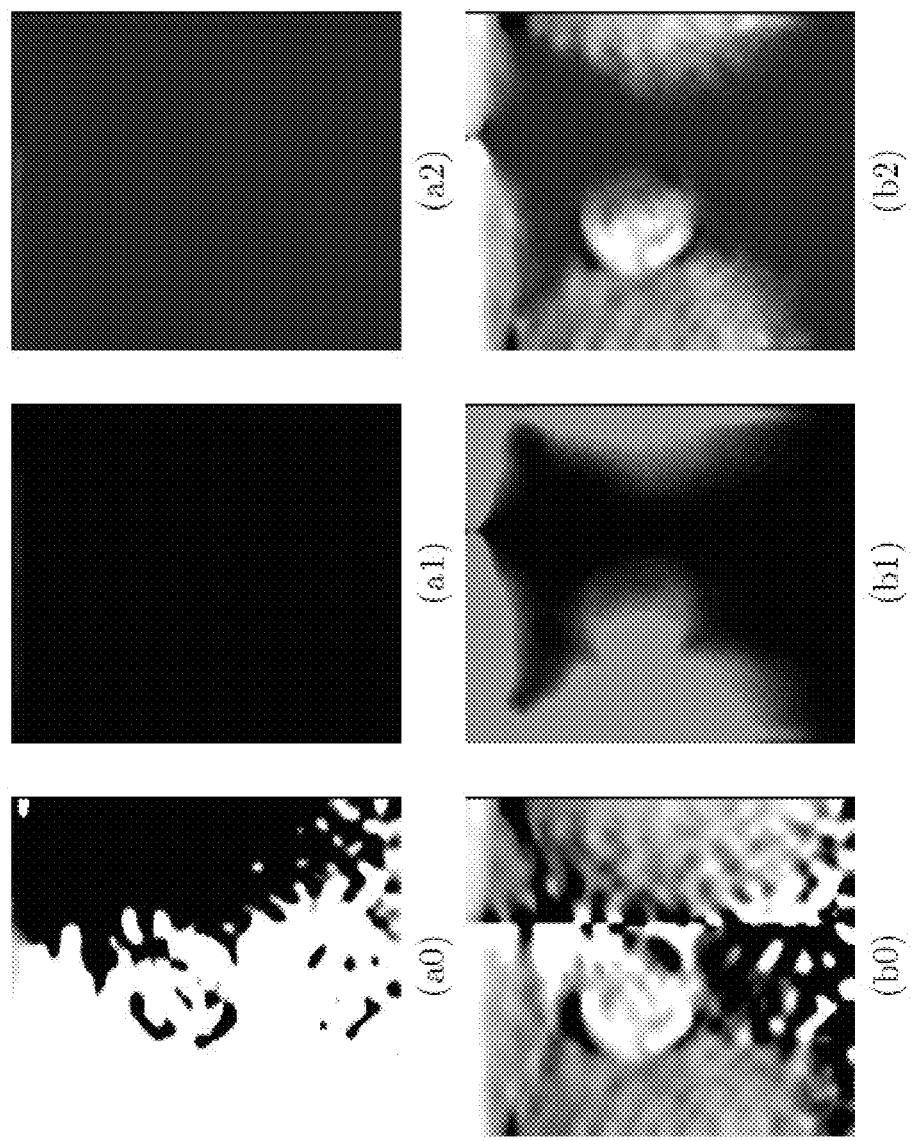
FIG. 8 records a frame in which the main motion has been rotational, so one side extends while the other compresses. The label 0 denotes use of a black-white colour map without precision data. (a) If a uniform normalisation is used the resulting pseudo-strain image has one half coloured white and the other black about a pivot. Fortunately the precision data correctly register an absence of useful data, so (a1) and (a2) are blank. However, the more sophisticated normalisation applied in (b) registers many useful measurements, with acceptable precision at the edges of the image, away from a central pivot, the position of which is clearly visible.

Rotational movement of the probe often results in stark differences depending on the form of the normalisation. The image in FIG. 8 is a relatively extreme example. This demonstrates the importance of appropriate normalisation for making best use of the recorded data.

Figure 9:
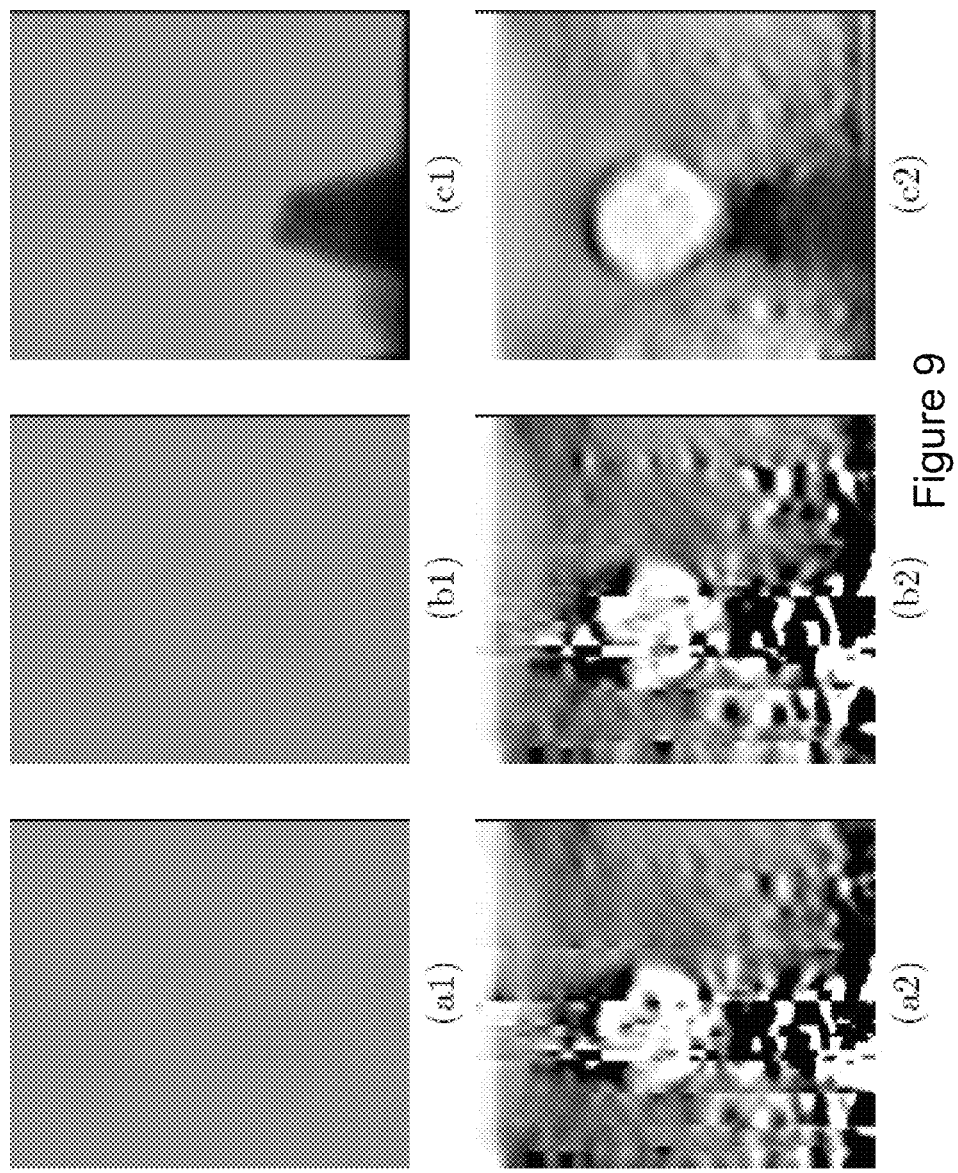
FIG. 9 shows examples of persistence alternatives applied to a sequence of strain images from the scan of the breast biopsy phantom, where the scan has been conducted inexpertly, frequently rolling the probe about the elevational axis. (a) Unweighted frame averaging still produces poor results. (b) In this instance precision-weighted frame averaging is no better than unweighted averaging, because the precision of each individual estimate correlates poorly with the mean precision in each frame. (c) Precision-weighted persistence at the pixel level produces a far better image.

The in homogeneity of pseudo-strain precision in these images means that they also highlight the value of correctly applying weighted persistence at the pixel-level. FIG. 9 shows that in this instance precision-weighted frame averaging is no better than unweighted frame averaging, whereas an excellent pseudo-strain image is produced by applying precision-weighted persistence at the level of individual pixels. Our sophisticated normalisation with lateral stress correction is advantageous because it both reduces the level of noise and produces a pseudo-strain image that corresponds much more closely to the stiffness of the phantom material.

Figure 10:
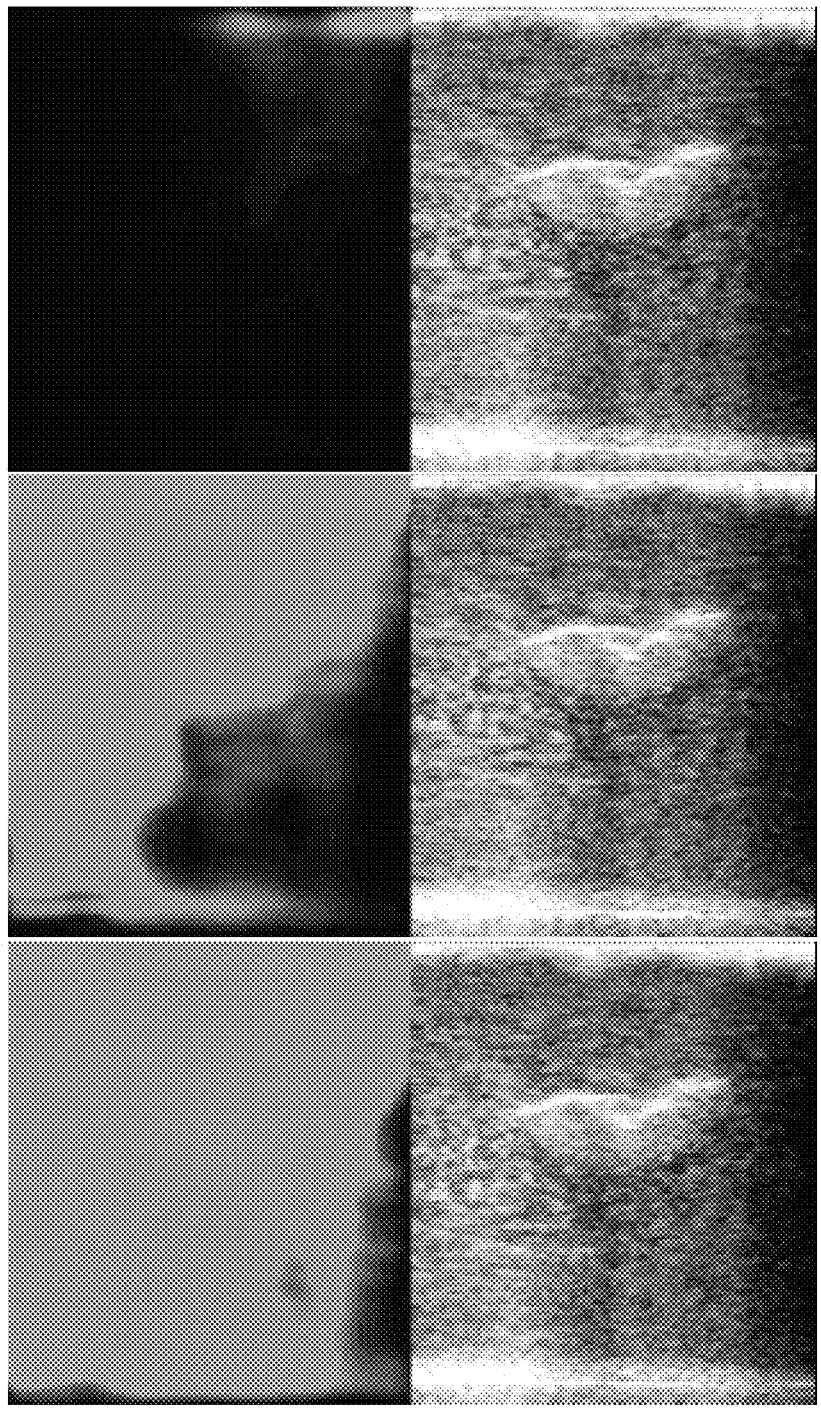
FIG. 10 shows a sequence of images at the start of a freehand scan.
Figure 10:
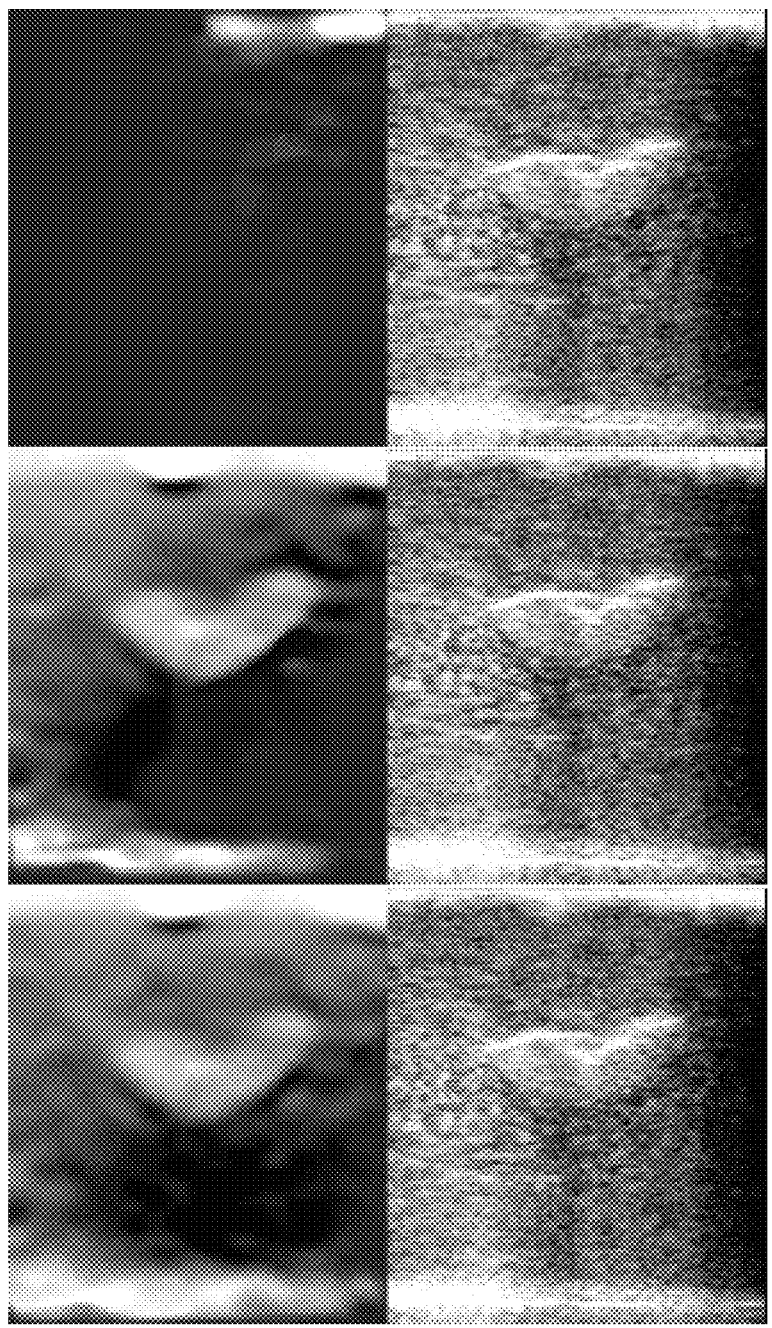

Finally, FIG. 10 shows a typical image sequence indicative of the sonographer's experience when beginning a freehand scan using the new interface. The scan target in this example is an inhomogeneous agar phantom containing half of an olive, which is slightly stiffer than the agar. The screen is initially black (or red) before acceptable data become available. It begins to colour almost immediately on contact with the scan target, although some parts of the image colour less quickly than others, while regions without data—such as the shadow on the right—may remain black/red. Stable images are achieved easily, and the development of a successful scanning technique is supported by visual feedback: good technique illuminates the display, whereas poor movements cause it to darken.

SUMMARY

We have described a novel interface for real time freehand strain imaging, with explanations of the underlying theoretical principles. The preferred inputs for the interface are strain estimates from a robust strain estimator, together with accurate precision estimates. This means that the interface can be incorporated as the front end on a wide range of strain imaging systems, although the best results are likely to be produced in systems that include robust displacement estimation that neither relies on exhaustive searching nor on tracking methods that exhibit excessive fragility.

Notable aspects of our interface include a normalisation stage, persistence or compounding and a novel display using a 2D colour map. Normalisation reduces the ambiguity of strain imaging, and actually reduces the level of noise in persisted images. It follows that good, informative pseudo-strain images can be produced by a wide range of probe motions, rather than relying heavily on careful, even compressions. In order to exploit these benefits fully, persistence should preferably be weighted at the level of individual pixels rather than at the level of sequential images.

This system not only improves the quality of the results from particular data sets, but it also supports the acquisition of suitable data, by helping the sonographer to develop a successful scanning technique. Wide-ranging clinical trials will begin mid-2007 in Addenbrooke's Hospital (Cambridge, UK) to investigate suitable applications for this system. Although the interface has already been received enthusiastically by our clinical collaborators, the best normalisation and 2D colour scheme may be application-dependent, so a range of application-specific settings may be within the existing interface structure.

No doubt many other effective alternatives will occur to the skilled person. It will be understood that the invention is not limited to the described embodiments and encompasses modifications apparent to those skilled in the art lying within the spirit and scope of the claims appended hereto.

The invention claimed is:

1. A method of displaying strain image data for an imaged object, the method comprising:
   capturing strain image data for a plurality of image frames, said strain image data defining deformation of said object over an imaged region of said object;
   determining local image quality data for each of said image frames, said local image quality data comprising a measure of the quality of said strain image data varying over said imaged region for said each image frame; and
   displaying a representation of said strain image data for said imaged region of said object, using said local image quality data to provide a visual indication of the quality of said displayed representation varying over said imaged region or to improve a quality of said displayed representation of said strain image data.

2. A method as claimed in claim 1 wherein said determining of said local image quality data comprises processing said strain image data to determine said local image quality data.

3. A method as claimed in claim 2 wherein said processing comprises determining displacement or strain data over said imaged region and associated error data, normalising said displacement or strain data over said imaged region, and normalising said error data using a normalisation value from said displacement or strain data normalising to provide said local image quality data.

4. A method as claimed in claim 3 wherein said imaged region comprises an at least one-dimensional region and wherein said normalising uses a normalisation which varies over said at least one dimension.

5. A method as claimed in claim 4 wherein said imaged region comprises an at least two-dimensional region in each image frame and wherein said normalising comprises fitting a tilted or curved surface to said displacement or strain data over said at least two-dimensional region in each image frame.

6. A method as claimed in claim 3 wherein said normalising of said displacement or strain data comprises determining a local normalisation factor for said displacement or strain data and wherein said normalising of said error data comprises scaling by said local normalisation factor squared.

7. A method as claimed in claim 1 wherein said capturing comprises capturing data for a plurality of image frames and wherein said displaying of said representation of said strain image data for said imaged region of said object comprises determining cumulative displacement or strain data for said imaged region of said object over a plurality of said image frames weighted by said local image quality data.

8. A method as claimed in claim 1 wherein said capturing comprises capturing data for a plurality of image frames and wherein said using of said image quality data comprises accumulating said local image quality data over a plurality of said image frames.

9. A method as claimed in claim 1 wherein said using of said local image quality data comprises using said local image quality data to provide a visual indication of the quality of said displayed representation varying over said imaged region.

10. A method as claimed in claim 9 wherein said displaying of a representation of said strain image data comprises displaying a pixellated representation of said strain image data, and wherein said determining of said local image quality data and said displaying of said visual individuation of said quality is performed on a per pixel basis.

11. A method as claimed in claim 9 wherein said representation of said strain image data for said imaged region of said object comprises a monochrome representation and wherein said visual indication of the quality of said displayed representation uses one or more colours.

12. A method as claimed in claim 9 wherein said visual indication of the quality of said displayed representation comprises reducing a brightness of said representation of said strain image data for said imaged region of said object where said quality of said displayed representation is relatively reduced.

13. A method as claimed in claim 9 wherein said displaying comprises encoding both said strain image data and said local image quality data in colour space.

14. A method of displaying strain image data for an imaged object, the method comprising:
   capturing strain image data for a plurality of image frames, said strain image data defining deformation of said object over an imaged region of said object;
   processing said strain image data to determine local image quality data for each of said image frames, said local image quality data comprising a measure of the quality of said strain image data varying over said imaged region for said each image frame; and
   displaying a representation of said strain image data for said imaged region of said object;
   wherein said displaying comprises determining cumulative displacement or strain data for said imaged region of said object over a plurality of said image frames weighted by said local image quality data.

15. A method as claimed in claim 14 wherein said displaying further comprises displaying a representation of variation over said imaged region of said local image quality data in combination with said representation of said strain image data.

16. A method as claimed in claim 15 wherein said displayed representation of said variation over said imaged region of said local image quality data is derived from said local image quality data for multiple image frames.

17. A method as claimed in claim 15 wherein said displaying of said combination of said local image quality data and said strain image data comprises encoding said combination in colour space.

18. A non-transitory computer readable medium having computer executable instruction for performing the method of claim 14.

19. Apparatus for displaying strain image data for an imaged object, the apparatus including a processor coupled to data memory and to program memory, said program memory storing instructions for controlling the processor to:
   capture strain image data for a plurality of image frames, said strain image data defining deformation of said object over an imaged region of said object;
   determine local image quality data for each of said image frames, said local image quality data comprising a measure of the quality of said strain image data varying over said imaged region for said each image frame; and
   display a representation of said strain image data for said imaged region of said object, using said local image quality data to provide a visual indication of the quality of said displayed representation varying over said imaged region or to improve a quality of said displayed representation of said strain image data.

20. Apparatus for displaying strain image data as claimed in claim 19 wherein said program memory further stores instructions for controlling the processor to process said strain image data to determine said local image quality data, and wherein said instructions to display a representation of said strain image data comprise instructions to use said local image quality data to provide a visual indication of the quality of said displayed representation varying over said imaged region.

21. Apparatus for displaying strain image data for an imaged object, the apparatus including a processor coupled to data memory and to program memory, said program memory storing instructions for controlling the processor to:

capture strain image data for a plurality of image frames, said strain image data defining deformation of said object over an imaged region of said object;

process said strain image data to determine local image quality data for each of said image frames, said local image quality data comprising a measure of the quality of said strain image data varying over said imaged region for said each image frame; and display a representation of said strain image data for said imaged region of said object;

wherein said display comprises determining cumulative displacement or strain data for said imaged region of said object over a plurality of said image frames weighted by said local image quality data.

22. Apparatus as claimed in claim 19 wherein said strain image data is derived by ultrasonic imaging.

23. A method as claimed in claim 1 wherein said strain image data is derived by ultrasonic imaging.

24. A non-transitory computer readable medium having computer executable instruction for performing the method of claim 1.

25. A method as claimed in claim 14 wherein said strain image data is derived by ultrasonic imaging.

26. Apparatus as claimed in claim 20 wherein said strain image data is derived by ultrasonic imaging.

27. Apparatus as claimed in claim 21 wherein said strain image data is derived by ultrasonic imaging.

28. A method according to claim 1, wherein said displaying comprises mapping a variation of local image quality over said imaged region in an image frame.

29. A method according to claim 14, wherein said displaying comprises mapping a variation of local image quality over said imaged region in an image frame.

30. Apparatus as claims in claim 19, wherein said displaying comprises mapping a variation of local image quality over said imaged region in an image frame.

* * * * *